US010564115B2

(12) United States Patent
Pals

(10) Patent No.: US 10,564,115 B2
(45) Date of Patent: Feb. 18, 2020

(54) X-RAY ANALYSIS OF DRILLING FLUID

(71) Applicant: Malvern Panalytical B.V., Almelo (NL)

(72) Inventor: Mark Alexander Pals, Almelo (NL)

(73) Assignee: MALVERN PANALYTICAL B.V., Almelo (NL)

( * ) Notice: Subject to any disclaimer, the term of this patent is extended or adjusted under 35 U.S.C. 154(b) by 289 days.

(21) Appl. No.: 15/586,465

(22) Filed: May 4, 2017

(65) Prior Publication Data

US 2017/0343495 A1  Nov. 30, 2017

(30) Foreign Application Priority Data

May 26, 2016  (EP) ..................................... 16171494

(51) Int. Cl.
*G01N 23/223* (2006.01)
*G01N 33/28* (2006.01)

(52) U.S. Cl.
CPC ....... *G01N 23/223* (2013.01); *G01N 33/2823* (2013.01); *G01N 2223/076* (2013.01); *G01N 2223/321* (2013.01); *G01N 2223/635* (2013.01); *G01N 2223/637* (2013.01)

(58) Field of Classification Search
CPC ....... G01N 2223/076; G01N 2223/321; G01N 2223/635; G01N 2223/637; G01N 23/223
See application file for complete search history.

(56) References Cited

U.S. PATENT DOCUMENTS

| 3,354,308 | A | * | 11/1967 | Engel | ................... | G01N 23/223 |
| | | | | | | 378/47 |
| 4,752,668 | A | * | 6/1988 | Rosenfield | ................ | G03F 1/72 |
| | | | | | | 219/121.68 |
| 5,721,759 | A | * | 2/1998 | Raatikainen | ......... | G01N 23/223 |
| | | | | | | 378/44 |
| 2004/0109534 | A1 | | 6/2004 | Uehara et al. | | |
| 2010/0046700 | A1 | | 2/2010 | Sakai et al. | | |
| 2011/0051894 | A1 | | 3/2011 | Takahara | | |
| 2012/0051507 | A1 | | 3/2012 | Hasegawa et al. | | |
| 2013/0235974 | A1 | | 9/2013 | Stock et al. | | |
| 2015/0118376 | A1 | * | 4/2015 | Huyzer | .................. | A01K 5/004 |
| | | | | | | 426/518 |
| 2016/0084718 | A1 | | 3/2016 | Teale | | |

FOREIGN PATENT DOCUMENTS

| JP | 2006-153767 | 6/2006 |
| JP | 2009-074934 | 4/2009 |
| JP | 2010-071969 | 4/2010 |

(Continued)

*Primary Examiner* — Chih-Cheng Kao
(74) *Attorney, Agent, or Firm* — Leason Ellis LLP

(57) ABSTRACT

A measurement head for making X-ray measurements on drilling fluid includes an inner pipe (30) having a outlet (32) and an outer pipe (34) around the inner pipe. Drilling fluid is pumped through the outlet refreshing the fluid at the outlet. The pump is then stopped. A height sensor (42) is then used to measuring the height of a meniscus of drilling fluid at the outlet (32). An X-ray head (50) including an X-ray source (52) and an X-ray detector (54) is then moved into a reproducible position above the meniscus of fluid above the outlet. The height sensor (42) may be fixed to a movable cover (40), to the X-ray head (50) or to some other part of the measurement head.

10 Claims, 4 Drawing Sheets

(56) References Cited

FOREIGN PATENT DOCUMENTS

| | | |
|---|---|---|
| JP | 2011-047898 | 3/2011 |
| JP | 2012-052817 | 3/2012 |
| JP | 2013-205081 | 10/2013 |
| JP | 2014-531531 | 11/2014 |
| WO | WO 1993/017326 | 9/1993 |
| WO | WO 96/015442 | 5/1996 |

* cited by examiner

X-RAY ANALYSIS OF DRILLING FLUID

CROSS-REFERENCE TO RELATED APPLICATIONS

The present application claims priority under 35 U.S.C. § 119 to European Patent Application No. 16171494.4, filed May 26, 2016, which is hereby incorporated by reference in its entirety.

FIELD OF INVENTION

The invention relates to a measurement head for making X-ray measurements on drilling fluid and a method of making X-ray measurements using such a measurement head. The invention also relates to a system including such a measurement head.

BACKGROUND TO THE INVENTION

There is an on-going need for measuring the content of drilling fluids, also known as drilling muds or drill muds. There may be a need to measure the content of fluid returning from the drill head, carrying sediment, or alternatively to measure the content of fluid sent to the drill head.

A method of measuring drilling fluids using X-ray fluorescence, XRF, is proposed in WO 1993/017326. However, this document is silent as to the experimental details of obtaining reproducible measurements from drilling fluids.

The reason this is important is that quantitative X-ray fluorescence is a technique that obtains data that is very highly dependent on the exact positions and orientations of the X-ray source, X-ray detector and sample. Even small deviations in distance between source and sample or between detector and sample can result in significant changes in the strength of X-ray fluorescence signals. For solid samples, it is less difficult to arrange for source, detector and sample to be in a very precisely known and reproducible position. There remains however a need to achieve the same accuracy with fluid samples.

An X-ray head used for measuring slurries (or liquids) is proposed in U.S. Pat. No. 3,354,308. Slurries are pumped through an inner pipe with an open end terminating in a larger pipe. A membrane closes off the larger pipe and X-ray measurements are made through the membrane using an X-ray source and a pair of X-ray detectors. However, there is no control of the exact position of the upper surface of the slurry which can vary, for example with changing composition, temperature or viscosity of the slurry and further the membrane can in some cases influence the measured results.

SUMMARY OF THE INVENTION

In accordance with a first aspect of the invention, there is provided a measurement head for drilling fluid, comprising:
  an inner pipe having an outlet, the outlet extending horizontally for allowing stationary fluid to remain in the pipe at the outlet for measurement;
  an outer pipe around the inner pipe for collecting material output by the outlet of the inner pipe;
  a height sensor for measuring the height of fluid at the outlet; and
  an X-ray head including an X-ray source and an X-ray detector;
  wherein the X-ray head is movable between a rest position and a measurement position wherein in the measurement position the X-ray source and X-ray detector are positioned above the outlet at a height determined by the height of fluid at the outlet measured by the height sensor.

With normal slurries, if the flow of the slurry is stopped the solid particles of the slurry rapidly segregate. Accordingly, it is not possible to stop the flow of the slurry and make measurements. However, the inventors have realised that drilling fluids are highly viscous materials, often with thixotropic properties, and so have different properties to conventional slurries, such that it is possible to stop the flow of the drilling fluid to take measurements.

With the fluid stopped, there will be a meniscus at the outlet. The height of the meniscus may vary slightly with the properties of the drilling fluid. By providing a measurement head with a height sensor for measuring the height of fluid at the outlet it is possible to precisely and reproducibly align the X-ray head above the outlet at a precise distance above the meniscus for accurate measurements.

By using a movable X-ray head it is also possible to get the X-ray source and X-ray detector close to the outlet during measurement and move them away during fluid flow.

Accordingly, the measurement head can deliver a precise X-ray measurement of drilling fluid.

The measurement head may include a cover movable between a first position covering the outlet to direct fluid output by the outlet into the outer pipe and at least one further position.

By providing a movable cover there is no need to make measurements through an X-ray permeable membrane closing off the outer pipe. Instead, a movable cover may cover the outlet while the drilling fluid is flowing through the inner pipe and the cover may be removed for measurement after the flow has stopped. It will be appreciated that a membrane must be thin and made of X-ray permeable material so the use of a movable cover makes for a more robust measurement head which improves reliability.

In one approach, the height sensor may be a laser height sensor mounted to the cover, wherein the cover is movable between the first position, a second position in which the laser height sensor is above the outlet to measure the height of material at the outlet and a third position in which neither the cover nor the laser height sensor are above the outlet.

In this way, the height of the meniscus of drilling fluid in the outlet can be accurately measured with the cover in the second position and this information used to accurately align the measurement head.

In particular, the X-ray head may be movable in the vertical direction with the cover in the third position so that the X-ray head can be moved to a position with an accurately reproducible height above material in the outlet using measurements from the laser height sensor.

In an alternative arrangement, the height sensor may be mounted to the X-ray head. The cover may be movable between the first position and a second position in which the cover is spaced from the outlet. The X-ray head may be movable in the vertical direction with the cover in the second position so that the X-ray head can be moved to a position with a fixed height above material in the outlet using measurements from the laser height sensor. The height sensor may be a light beam occlusion sensor having a light source and a light detector, the light source directing a light beam onto the light detector; wherein the X-ray head is moved downwards until the light beam incident on the light detector is broken. Such height sensors are relatively inexpensive but can nevertheless achieve very accurate reproducibility of height of the X-ray head above fluid in the outlet.

The height sensor may also comprise a camera for capturing an image of the height of fluid at the outlet.

In another aspect, the invention also relates to a measurement system, having a measurement head as discussed above and a control means arranged to control the motion of the X-ray head and height sensor. The control means may be in the form of a bespoke controller and/or computer software arranged to run on a general purpose computer.

In another aspect, the invention relates to a method of operation of a measurement head for drilling fluid, comprising:
- pumping drilling fluid through an inner pipe, out through a outlet and removing the drilling fluid from the outer pipe;
- halting the pumping leaving a meniscus of drilling fluid at the outlet;
- using the height sensor to measure the height of the meniscus;
- aligning the X-ray head using the measured height; and
- making an X-ray measurement using the X-ray head.

By halting the pumping a stationary meniscus of drilling fluid is provided. The height sensor can then be used to very accurately position the X-ray head with respect to the stationary meniscus to achieve accurate X-ray measurements.

The X-ray measurements may in particular be X-ray fluorescence measurements.

The method may also include covering the outer pipe over the outlet with a movable cover during the step of pumping drilling fluid; and moving the movable cover during the steps of using the height sensor, aligning the X-ray head and making an X-ray fluorescence measurement. In this way, it is possible to remove the cover necessary to stop the drilling fluid escaping from the outer pipe to get the X-ray head close to and directly above the meniscus at the outlet for accurate measurements.

The height sensor may be a laser height sensor mounted to the cover, wherein the movable cover is in a first position during the step of pumping drilling fluid. The method may include:
- moving the cover to a second position in which the laser height sensor is above the outlet during the step of measuring the height of material at the outlet; and
- moving the cover to a third position in which neither the cover nor the laser height sensor are above the outlet during the steps of aligning the X-ray head and making an X-ray fluorescence measurement.

The method may also include moving the X-ray head in the vertical direction with the cover in the third position to a position with a fixed height above material in the outlet using measurements from the laser height sensor.

The height sensor may be mounted to the X-ray head. The steps of using a height sensor and aligning the X-ray head take place at the same time by moving the X-ray head in the vertical direction until it reaches a position with a fixed height above material in the outlet using measurements from the laser height sensor.

The height sensor may be a light beam occlusion sensor having a light source and a light detector, the light source directing a light beam onto the light detector. The method may include moving the X-ray head downwards until the light beam incident on the light detector is broken.

BRIEF DESCRIPTION OF THE DRAWINGS

An example of the invention will now be described with reference to the accompanying diagrams, in which.

The Figures are schematic and not to scale.

DETAILED DESCRIPTION

Figure 1:
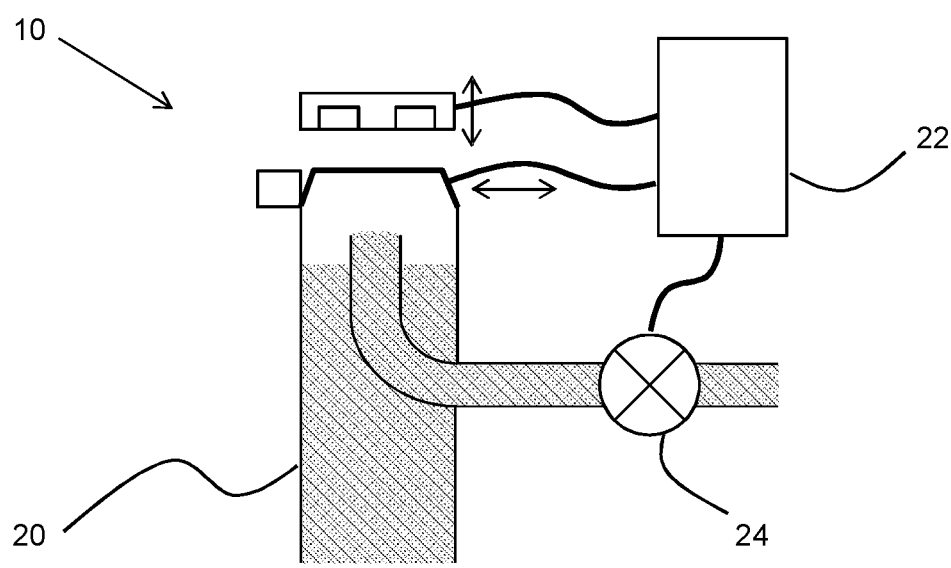
FIG. 1 is a schematic view of a measurement system

FIG. 1 illustrates a measurement system (10) having a measurement head (20) intended for measuring drilling fluid, also known as drilling mud and a control system (22). A pump (24) controlled by the control system (22) is connected to pump drilling fluid to the measurement head.

Figure 2:
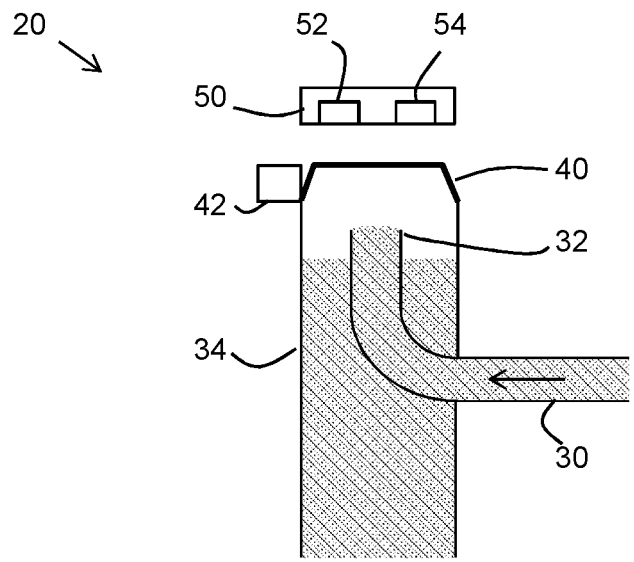
FIG. 2 is a schematic view of the measurement head of the measurement system of FIG. 1 in a pump mode.
Figure 3:
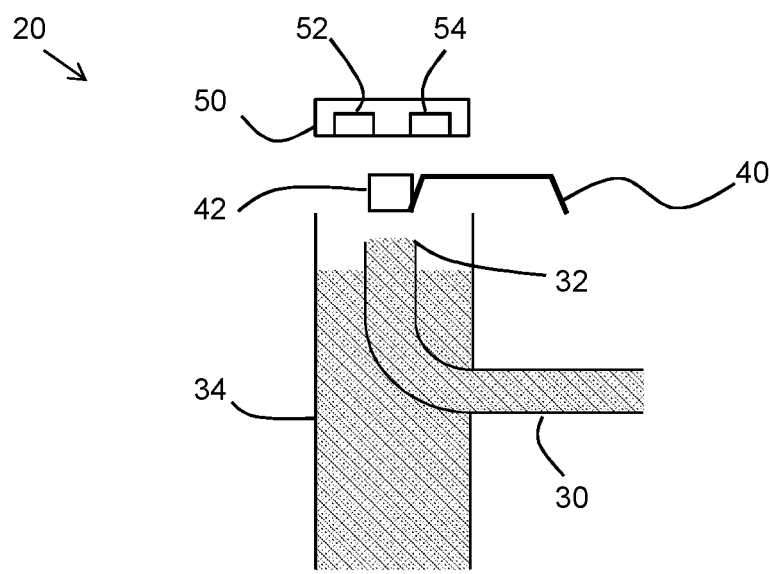
FIG. 3 is a schematic view of the measurement head of the measurement system of FIG. 1 in a height measurement mode.
Figure 4:
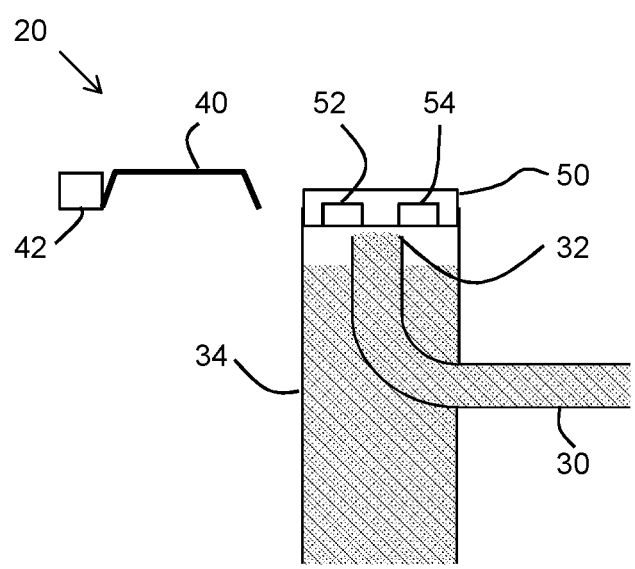
FIG. 4 is a schematic view of the measurement head of the measurement system of FIG. 1 in a XRF measurement mode.

Referring to FIGS. 2 to 4, the measurement head (20) has an inner pipe (30) for connection to the pump (24). The inner pipe has a outlet (32) to provide a flat surface of drilling fluid for measurement. In particular, the outlet may be a horizontal outlet so that in use a fluid in the inner pipe can rest with a horizontal meniscus at the outlet in the inner pipe for measurement.

An outer pipe (34) is provided around the outlet that provides an outlet for drilling fluid.

A movable cover (40) is provided with multiple positions. In the embodiment shown in FIGS. 1 to 4, the cover has three positions, namely a pump position (FIG. 2), a height measurement position (FIG. 3) and an X-ray fluorescence XRF measurement position (FIG. 4). A laser height sensor (42) is fixed to the cover: in the height measurement position (FIG. 3) the laser height sensor (42) is directly over the outlet (32).

An X-ray head (50) includes an X-ray source (52) and an X-ray sensor (54). The X-ray head (50) has two positions, a retracted position (FIGS. 2 and 3) and an XRF measurement position (FIG. 4) in which the cover is fully retracted and the X-ray head (50) is directly above the outlet (32).

In use, in a pump mode (FIG. 2) drilling fluid is pumped continuously through the inner pipe (30) and out the outlet (32). The drilling fluid hits the cover (40) and falls back down to the outer pipe (34). The drilling fluid is then fed back into the drilling process. In this mode, the system is not making any measurements but simply continuously refreshing the drilling fluid within the measurement system (10).

To carry out a measurement, in a height measurement mode (FIG. 3) the pump is stopped. Material that remains in the inner pipe forms a meniscus at the outlet (32). The cover (40) moves so that the laser height sensor (42) is directly above the outlet. The laser height sensor measures the exact height of the meniscus and feeds the information back to the control system (22).

Then, the cover is fully retracted in an XRF measurement mode (FIG. 4). The control system (22) lowers the X-ray head (50) to a position with an exact, known distance above the measured height of the meniscus. The X-ray source generates X-rays incident on the drilling fluid sample within the outlet (32) and detects the generated fluorescence characteristic of materials in the drilling fluid.

In this way, it is possible to accurately align the X-ray head with the top of the meniscus at a fixed, short distance. Accurate alignment is very important for the reproducibility of XRF measurements—even small deviations in the distance between the X-ray head and the meniscus between different measurements can give rise to severe measurement errors making quantitative XRF impossible.

Typically, the X-ray head will be aligned approximately 1 mm above the meniscus, for example 0.2 mm to 3 mm, but the exact height can be selected differently if required. The important point is that the height is exactly reproducible for accurate and reproducible XRF measurement.

The inventors have realised that the properties of drilling fluids makes this approach possible. For typical slurries it is necessary to make XRF measurements while the slurry is in motion, since slurries start to segregate very quickly. This in turn makes it difficult to accurately align the measurement head with the slurry, since the fact that the slurry is in motion means that the exact position of the slurry will inevitably not be fixed. In contrast, drilling fluids segregate slowly, in comparison with the time to measure the meniscus height and carry out the XRF measurement, so it is possible to stop the pump, measure the height of the stationary meniscus, position the X-ray head and make an XRF measurement in significantly less than the time for the drilling fluid to segregate.

Figure 5:
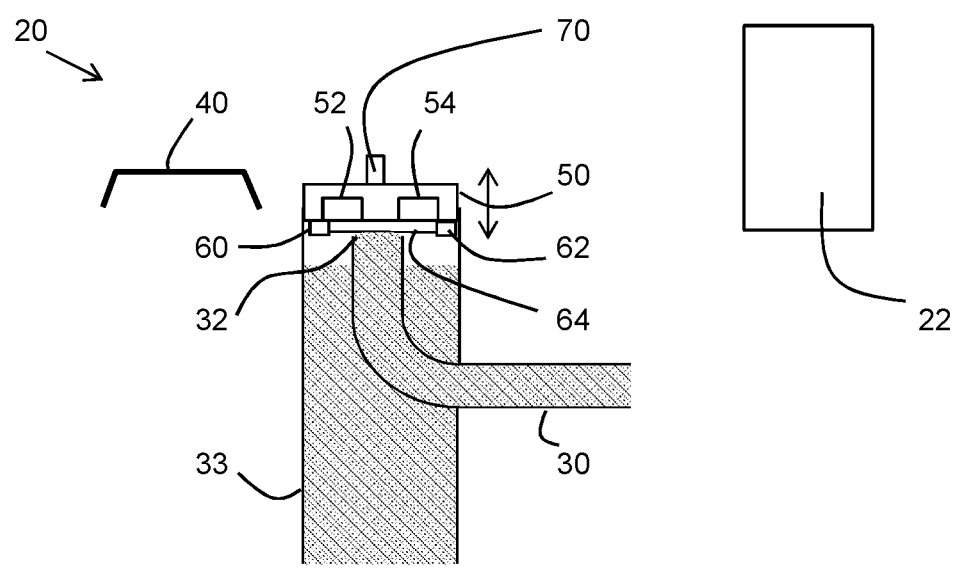
FIG. 5 is a schematic view of an alternative measurement head in a measurement mode.

In an alternative embodiment, illustrated in FIG. 5, a different laser height measurement system is adopted. In this case, the laser height measurement system is fixed to the X-ray head (50), not the cover (40). The laser height measurement system includes a laser source (60) emitting a laser beam (64) directed to a photocell detector (62). Normally, the beam (64) from the laser source (60) is incident on the photocell detector (62) but in the event that material interrupts the light beam this is detected. The sensors (60,62), cover (40) and additional components are connected to controller (22)—for clarity these connections—typically electrical—are not shown in FIG. 5.

In use, the pump mode operates as in the embodiment of FIG. 2 above. In the height measurement mode, the cover (40) is fully retracted and then the control system (22) lowers the X-ray head (50) downwards towards the meniscus on the outlet (32) until the meniscus (or outlet) interrupts the laser beam which is detected by the photocell detector (54). The motion of the X-ray head is immediately stopped leaving the X-ray head at a precise and repeatable position above the meniscus.

At this point, the XRF measurement mode begins and the X-ray head is used to make a measurement.

Alternatively or additionally, a camera (70) may be provided to capture an image of the meniscus on the outlet. In the embodiment of FIG. 5, this is an additional camera but in alternative arrangements the camera (70) may be used alone as a height sensor with the processor (22) arranged with height calculation software to calculate the height of the meniscus from the image. The camera position may be adapted to allow such measurements, for example by fixing the camera to the X-ray head in an orientation such that with the X-ray head in the measurement position the camera is positioned to take an image of the meniscus from the side.

Those skilled in the art will realise that alternative implementations are possible.

Although the above description is focused on XRF measurement, the system may also be applied to X-ray diffraction analysis. This may in particular be useful where small crystalline particles are present in the drilling fluid.

Although the above description is focused on drilling fluids, the apparatus and method may also be used for other fluid materials with similar properties, in particular liquid—solid mixtures such as slurries in the case where long segregation times make it possible to stop fluid pumping to take a measurement.

A variety of different types of height sensors may be used, which may be fixed as convenient to the cover, X-ray head or alternatively fixed with respect to the outer pipe.

Any convenient X-ray source and detector may be used—the exact choice may depend on the application.

The invention claimed is:

1. A measurement head for drilling fluid, comprising:
   an inner pipe having an outlet, the outlet extending horizontally for allowing stationary fluid to remain in the inner pipe at the outlet for measurement;
   an outer pipe around the inner pipe for collecting material output by the outlet of the inner pipe;
   a height sensor for measuring the height of fluid at the outlet;
   an X-ray head including an X-ray source and an X-ray detector; and
   a cover movable between a first position covering the outlet to direct fluid output by the outlet into the outer pipe and a second position in which the cover is spaced from the outlet;
   wherein the X-ray head is movable in the vertical direction with the cover in the second position so that the X-ray head can be moved to a position with a fixed height above material in the outlet using measurements from the height sensor; and
   wherein the height sensor is a light beam occlusion sensor having a light source and a light detector, the light source directing a light beam onto the light detector; and
   wherein the X-ray head is arranged to be moved downwards until the light beam incident on the light detector is broken.

2. A measurement head according to claim 1, wherein the height sensor comprises a camera for capturing an image of the height of fluid at the horizontal output.

3. A measurement system, comprising:
   a measurement head comprising:
      an inner pipe having an outlet, the outlet extending horizontally for allowing stationary fluid to remain in the pipe at the outlet for measurement;
      an outer pipe around the inner pipe for collecting material output by the outlet of the inner pipe;
      a height sensor for measuring the height of fluid at the outlet; and
      an X-ray head including an X-ray source and an X-ray detector; and
   a control means arranged to control the motion of the X-ray head and height sensor to move the X-ray head between a rest position and a measurement position, wherein in the measurement position the X-ray source and X-ray detector are positioned above the outlet at a height determined by the height of fluid at the outlet measured by the height sensor,
   and wherein the height sensor is a light beam occlusion sensor having a light source and a light detector, the light source directing a light beam onto the light detector; and
   wherein the X-ray head is arranged to be moved downwards until the light beam incident on the light detector is broken.

4. A method of operation of a measurement head for drilling fluid, comprising:

pumping drilling fluid through an inner pipe, out through a outlet and removing the drilling fluid from an outer pipe;

halting the pumping, leaving a meniscus of drilling fluid at the outlet;

using a height sensor to measure the height of the meniscus;

aligning an X-ray head using the measured height; and making an X-ray measurement using the X-ray head.

5. A method of operation according to claim 4, further comprising:

covering the outer pipe over the outlet with a movable cover during the step of pumping drilling fluid; and moving the movable cover before the steps of using the height sensor, aligning the X-ray head and making an X-ray fluorescence measurement.

6. A method of operation according to claim 5, wherein the height sensor is a laser height sensor mounted to the cover, wherein the movable cover is in a first position during the step of pumping drilling fluid, the method further comprising:

moving the cover to a second position in which the laser height sensor is above the outlet during the step of measuring the height of material at the outlet; and moving the cover to a third position in which neither the cover nor the laser height sensor are above the outlet during the steps of aligning the X-ray head and making an X-ray fluorescence measurement.

7. A method of operation according to claim 6 further comprising moving the X-ray head in the vertical direction with the cover in the third position to a position with a fixed height above material in the outlet using measurements from the laser height sensor.

8. A method of operation according to claim 5, wherein the height sensor is mounted to the X-ray head;

wherein the steps of using a height sensor and aligning the X-ray head take place at the same time by moving the X-ray head in the vertical direction until it reaches a position with a fixed height above material in the outlet using measurements from the height sensor.

9. A method of operation according to claim 8, wherein the height sensor is a light beam occlusion sensor having a light source and a light detector, the light source directing a light beam onto the light detector;

the method comprising moving the X-ray head downwards until the light beam incident on the light detector is broken.

10. A method of operation according to claim 4, wherein the X-ray measurements are X-ray fluorescence measurements.

* * * * *